United States Patent [19]

Stults et al.

[11] Patent Number: 5,185,471

[45] Date of Patent: Feb. 9, 1993

[54] METHOD FOR ETHER FORMATION

[75] Inventors: Jeffrey S. Stults; Robert A. Buchanan, both of Grand Island, N.Y.

[73] Assignee: Occidental Chemical Corporation, Niagara Falls, N.Y.

[21] Appl. No.: 797,584

[22] Filed: Nov. 25, 1991

Related U.S. Application Data

[63] Continuation-in-part of Ser. No. 669,707, Mar. 15, 1991, abandoned.

[51] Int. Cl.$^5$ .............................................. C07C 41/01
[52] U.S. Cl. ...................................................... 568/586
[58] Field of Search ................................. 568/585, 586

[56] References Cited

U.S. PATENT DOCUMENTS 4,558,164 12/1985 Jones et al. ...................... 568/585
4,700,011 10/1987 Pillsbury ............................ 568/585

FOREIGN PATENT DOCUMENTS 24125 2/1980 Japan ................................... 568/585

OTHER PUBLICATIONS

Mari et al., Gov. Industrial Research Institute, No. 3, 675–677, "Synthesis of Diisobyanates of Trifluoromethyl Substituted Biphenyls and Diphenyls", 1972.
Jacobs, J. Org. Chem., vol. 36, No. 1, pp. 242–243, 1971, "Synthesis of Nitrotrifluoromethylphenols and Related Compounds...".

Primary Examiner—Marianne M. Cintins
Assistant Examiner—Margaret J. Page
Attorney, Agent, or Firm—Wayne A. Jones; Richard D. Fuerle

[57] ABSTRACT

A process for the preparation of 1,1'-oxy-bis(3-trifluoromethyl-4-nitrobenzene) which comprises reacting a compound of the formula

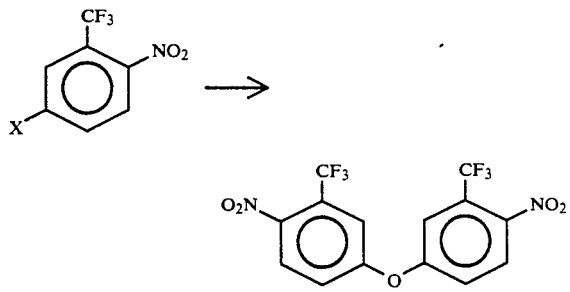

where X is F, Cl, Br or I; with an inorganic base selected from the group consisting of alkali metal hydroxides, alkali metal carbonates, and alkali metal bicarbonates, in the presence of a catalytic quantity of a benzoate catalyst. In addition, benzoate esters of 4-nitro-3-trifluoromethylphenol may be isolated.

11 Claims, No Drawings

METHOD FOR ETHER FORMATION

BACKGROUND OF THE INVENTION

This application is a continuation-in-part of U.S. application Ser. No. 07/669,707, filed Mar. 15, 1991, and now abandoned.

This invention relates to a method of forming 1,1'-oxy-bis(3-trifluoromethyl-4-nitrobenzene) from 5-halo-2-nitrobenzotrifluorides. 1,1'-Oxy-bis(3-trifluoromethyl-4-nitrobenzene) is useful as an intermediate in the production of 1,1'-oxy-bis(3-trifluoroacetyl-4-aminobenzene). This diamine is useful as a monomer in the production of polyimide resins. More particularly, it relates to the use of benzoic acid, substituted benzoic acids, and benzoate esters to catalyze the condensation of two molecules of an aryl halide to yield the diaryl ether.

Aryl ethers have been formed by reacting aryl halides with phenols under various conditions. Roberts and Turner disclose (J. Chem. Soc., 1925, 127, p. 2004) that 2,4-dichloronitrobenzene reacts with phenol in aqueous KOH, at 100° C., to give a quantitative yield of 4-chloro-2-phenoxynitrobenzene.

R.Q. Brewster (Org. Synth. Coll. Vol. 2, p. 445, 1943) teaches the use of a copper catalyst to facilitate the reaction of excess phenol, potassium hydroxide and para-nitrochlorobenzene to form para-nitrophenyl phenyl ether.

J.D. Reinheimer et al, disclose (J. Org. Chem., 1957, vol. 22, p. 1743) that 2,4-dinitrofluorobenzene reacts with 8-hydroxyquinoline in acetone, in the presence of triethylamine, to form 8-(2,4-dinitrophenoxy)quinoline.

D.J. Brunelle and D.A. Singleton disclose (Tetrahedron Lett., 1984, 25, p. 3383) that the reaction between sodium phenoxide and either para-fluoronitrobenzene or para-chloronitrobenzene, to form para-nitrophenyl phenyl ether may be conducted in chlorobenzene using a phase transfer catalyst. In this case, the phase transfer catalysts studied were N-alkyl salts of 4-dialkylamino pyridines.

Singh and Arora disclose (Tetrahedron 1988, 44, p 2625) that para-chloronitrobenzene dissolved in toluene may be reacted with solid potassium hydroxide to form 4,4'-dinitrodiphenyl ether. The authors observed the reaction only in the presence of catalytic quantities of various glycols. The authors indicate that the glycols act as phase transfer catalysts. The yields of the ether were poor, that is, never higher than 25%, and there was significant formation of para-chloroaniline. The authors performed mechanistic studies which led them to the conclusion that the reaction proceeded by a free radical chain mechanism.

U.S. Pat. No. 4,558,164 discloses a process for preparing a symmetrical dinitrophenyl ether from either ortho or para-nitrochlorobenzene or ortho or para-nitrofluorobenzene, comprising using a polar organic solvent, a potassium salt of a fatty carboxylic acid containing 2 to 20 carbon atoms or a potassium salt of an aromatic carboxylic acid containing 7 to 12 carbon atoms as catalyst, and either sodium or potassium carbonate to react with the para-nitrochlorobenzene. The reaction is carried out at from 150° C. to 210° C. until the ortho or para-nitrochlorobenzene or ortho or para-nitrofluorobenzene reacts. Only aprotic polar solvents are useful and dimethylacetamide is the preferred solvent.

Japanese Patent 61200947 (as abstract in CA 106:156046 and in Derwent Accession number 86-275567/42) discloses a process for the preparation of 3,4'- and 4,4'-dinitrodiphenyl ether. In this process 4-chloronitrobenzene is mixed with a nitrophenol, a hydrogen chloride absorbent such as an alkaline metal hydroxide or bicarbonate, in the presence of 5 to 50 weight percent of the total material of polyethylene glycol of molecular weight 400 to 1000 or its lower alkyl ethers. The entire mixture is heated to a temperature being between 100 and 240° C. There is no additional solvent material used.

Maki and Inukai (Gov. Ind. Res. Inst. Nagoya, Nagoya, Japan Nippon Kagaku Kaishi (3), 675-7 (Japan) 1972) condensed chloronitrobenzotrifluorides with alkali metal carbonates to produce bis-trifluoromethyldinitrophenyl ethers. Specifically, they used 2-chloro-5-nitrobenzotrifluoride to produce the corresponding trifluoromethyl nitrodiphenyl ether. They also studied 5-chloro-2-nitrobenzotrifluoride. In order to accomplish the condensation, they used alkali metal carbonates in 1,3-dimethyl-2-imidazolidinone (DMI). No yields or other experimental details were reported.

In our own laboratories we found that the simple reaction of 2-chloro-5-nitrobenzotrifluoride with potassium carbonate led to side reactions. Various reactions were conducted in polar solvents such as DMAC (at 140°-150° C.) or non-polar solvents, or even neat in the presence of phase transfer catalysts (18-crown-6, tetraphenyl phosphonium bromide, or the methyl ethers of polyethylene glycols) at temperatures over 200° C. Unfortunately, an appreciable quantity of products such as 2-fluoro-5-nitrobenzotrifluoride were formed. Since there is no other source of fluorine, the appearance of these products indicated that there was some decomposition of the trifluoromethyl group.

Jacobs discloses (Journal of Organic Chemistry v. 36; p. 242; 1971) that when 4-nitro-3-(trifluoromethyl)-chlorobenzene (this molecule may also be named 5-chloro-2-nitrobenzotrifluoride) is treated with sodium hydroxide in dimethyl sulfoxide (DMSO), the trifluoromethyl group is completely removed and the product is 5-chloro-2-nitrophenol which is isolated in 93% yield.

Chaw, Fischer, and Happer (J. Chem. Soc. (B) 9, 1918-19, 1971), disclose the synthesis of the benzoate ester of 4-nitro-3-(trifluoromethyl)-phenol ($\alpha,\alpha,\alpha$-trifluoro-m-cresol benzoate by the reaction of $\alpha,\alpha,\alpha$-trifluoro-m-cresol with benzoyl chloride in pyridine.

SUMMARY OF THE INVENTION

It has now been found that substituted benzoic acids, and substituted benzoates, when present in catalytic quantities, catalyze the reaction of 5-halo-2-nitrobenzotrifluoride with an inorganic base and water to form 1,1'-oxy-bis(3-trifluoromethyl-4-nitrobenzene). In addition, if benzoate is present in sufficient quantity, benzoate esters of 4-nitro-3-(trifluoromethyl)phenol are formed. The reaction may be run in the absence of a solvent, or in a non-polar solvent in the presence of a phase transfer catalyst.

DESCRIPTION OF THE INVENTION

Surprisingly, we have now found that benzoate catalysts, that is, hydrolyzable benzoate esters, benzoic acid and its salts and substituted benzoic acids, and their salts, with substituents which are stable under the reaction conditions, when present in catalytic quantities, catalyze the reaction of 5-halo-2-nitro-benzotrifluoride and an inorganic base such as sodium carbonate, to form 1,1'-oxy-bis(3-trifluoromethyl-4-nitrobenzene). As set forth more fully below, the substituted benzoic acids may have either electron donating or electron withdrawing substituents. In addition, if benzoic acid or a substituted benzoic acid is used as a catalyst and is present in sufficient quantities, benzoate esters of 4-nitro-3-trifluoromethylphenol are formed by the displacement of the halide by the benzoate anion. These benzoate esters are useful as catalysts for the reaction of the present invention. Thus, the isolated ester may be used as the benzoate catalyst in running the reaction to convert 5-halo-2-nitrobenzotrifluoride to 1,1'-oxy-bis(3-trifluoromethyl-4-nitrobenzene). The halogen in the starting material may be F, Cl, Br or I. The starting material may be prepared by the nitration of a 3-halobenzotrifluoride. The chloro compound, that is 5-chloro-2-nitrobenzotrifluoride, is commercially available.

The reaction is run between about 110° C. and 220° C. The overall equation for the formation of the ether is:

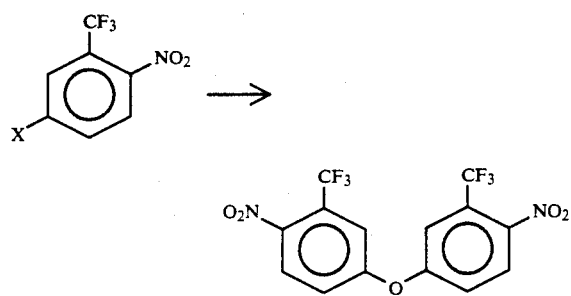

and the overall equation for the formation of esters is

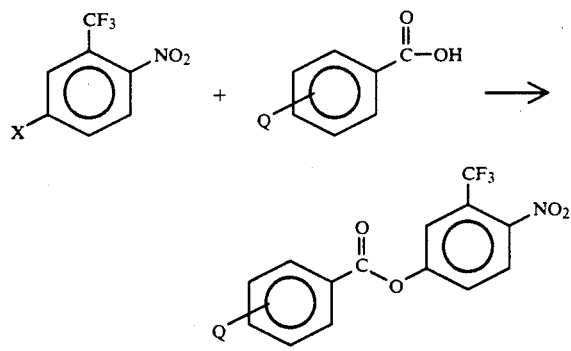

where X is F, Cl, Br, or I, and Q is any substituent or substituents suitable in a benzoate catalyst, for example, H, Cl, Bn, F, di-Cl$_2$, di-Bn$_2$, di-F$_2$, tri-Cl, tri-Bn, tri-F$_3$, CF$_3$, NO$_2$, di-(NO$_2$), R, RO, and R$_2$CO$_2$, where R is an alkyl group containing 1–12 carbon atoms and R$_2$ is an alkyl group containing 1–11 carbon atoms.

The reaction may be conducted in a non-polar solvent with a boiling point of greater than about 150° C. Alternatively the reaction may be run in a non-polar solvent of lower boiling point provided that it is run under sufficient pressure to achieve the temperatures necessary for the reaction. Among the non-polar solvents which may be used are aromatic hydrocarbons such as benzene, toluene, xylene, and chlorinated aromatic hydrocarbons such as trichlorobenzene, dichlorobenzene and α-chloronaphthalene.

A phase transfer catalyst, such as the methyl ether of polyethylene glycols, crown ethers, phosphonium salts, or ammonium salts is required. Generally speaking, a phase transfer catalyst is a chemical species which combines, within the same molecule both a polar and a non-polar end. Such molecules allow polar species to exist in non-polar solvents. The reaction may be conducted in the absence of a solvent using a phase transfer catalyst and conditions similar to those used for a non-polar solvent.

Whatever solvent is chosen for the reaction, a small amount of water is required for the reaction to proceed. However, water generally need not be added to the reaction since either the base, or the ingredients themselves, generally contain sufficient water for the reaction to occur. Accordingly, the addition of extra water is hardly ever necessary.

Alkali metal hydroxides, carbonates, and bicarbonates are suitable bases for conducting this reaction. The carbonates are the preferred bases. Although potassium carbonate and sodium carbonate are usable, cost considerations make sodium carbonate the preferred base. The choice of which benzoate to use is influenced by the base chosen for the reaction. For example, if carbonate is chosen as the base, then the reaction is best catalyzed by benzoates with moderately electron withdrawing constituents such as chlorine. On the other hand, when hydroxides are chosen as the base, electron rich benzoates, such as 4-methoxybenzoic acid, are useful catalysts. Whatever base is selected, it is important that a stoichiometric amount of base, or less, be used. Larger amounts of base may lead to side reactions, and, accordingly, are undesirable. It may also be desirable to add the base incrementally rather than in one portion in order to avoid side reactions. Any benzoate catalyst which is stable under the reaction conditions may be used as a catalyst for this reaction. For example, benzoic acid, chlorobenzoic acids, bromobenzoic acids, fluorobenzoic acids, dichlorobenzoic acids, dibromobenzoic acids, difluorobenzoic acid, tribromobenzoic acids, trichlorobenzoic acids, trifluorobenzoic acid, trifluoromethylbenzoic acids, nitrobenzoic acids, dinitrobenzoic acids, C1–C12 alkylbenzoic, C1–C12 alkoxybenzoic acids and C2–C12 acyloxybenzoic acids or salts of any of the above acids may be used as catalysts for this reaction. Among the hydrolyzable benzoate esters which may be used are alkyl benzoates of the acids set forth above and benzoate and substituted benzoate esters of 4-nitro-3-trifluoromethyl phenol. The catalyst is effective in amounts of about 0.1 mole % or more.

The catalytic effect of the benzoate is illustrated by comparing a reaction run without benzoate, with a similar reaction run in the presence of a benzoate. This can be readily seen by examining the results shown in Comparative Example 1, compared to the results shown by Examples 1–4. The comparative example, run without benzoate catalyst, shows much poorer yields and slower conversion than is shown by the same reaction run with benzoate. For example, in Example 1, after 3.5 hours of reaction there was 62% conversion whereas in Comparative Example 1 after the same time there was only 30.4% conversion. Similarly, Comparative Example 2 may be compared to Example 2. In Example 2, after 1.5 hours, there was 11.9% conversion and, in the absence of catalyst in Comparative Example 2, there was 0.2% conversion.

Formation of the ester can be increased by conducting the reaction in the presence of a minimal amount of water, by limiting the amount of base, or by using the salt of the benzoic acid as a reagent. Yields of the benzoyloxy esters can be maximized and the amount of the ether minimized by using a stoichiometric amount of the benzoic acid salt in the absence of additional base.

The product of this reaction may be isolated by filtering the reaction mixture to remove inorganic matter and evaporating the solvent. The resulting product may be crystallized from an alcohol such as methanol or ethanol. Other methods of isolation and purification will be apparent to those skilled in the art.

EXAMPLE 1

1,1'-Oxy-bis(3-trifluoromethyl-4-nitrobenzene) (OBTNB)

5-chloro-2-nitrobenzotrifluoride (CNBTF) (4.6 g, 20 mmol), potassium 4-chlorobenzoate (0.18 g, 1.0 mmol, 5 mole %), 18-crown-6 (0.19 g, 0.71 mmol), and potassium carbonate (1.34 g, 10 mmol) were heated to 130°–135° C. The reaction was monitored by GC area percent with the results shown below.

| Time | GC Area Percent | | |
|---|---|---|---|
| | CNBTF* | OBTNB** | Conversion |
| 0.5 hrs | 86.5 | 8.20 | 8.7% |
| 2.0 hrs | 60.3 | 31.7 | 35% |
| 3.5 hrs | 33.9 | 54.9 | 62% |

*CNBTF = 5-chloro-2-nitrobenzotrifluoride
**OBTNB = 1,1'-oxy-bis(3-trifluoromethyl-4-nitrobenzene)

The material was dissolved in refluxing toluene (15 mL) and filtered to remove salts. The solution was allowed to cool to room temperature and the resulting solid was collected, washed, and dried to give 1,1'-oxy-bis(3-trifluoromethyl-4-nitrobenzene) as a solid (2.0 g). GS-ISTD analysis of the mother liquor indicated an additional 0.7 g of product was present for a total yield of 2.7 g (67% yield, >95% yield based on conversion). Compare to Comparative Example 1.

EXAMPLE 2

1,1'-Oxy-bis(3-trifluoromethyl-4-nitrobenzene)

5-Chloro-2-nitrobenzotrifluoride (4.6 g, 20 mmol), sodium 3-nitrobenzoate, hemihydrate (0.20 g, 1.0 mmol, 5 mole %), 18-crown-6 (0.19 g, 0.71 mmol), potassium carbonate (1.33 g, 10 mmol), and 1,2,4-trichlorobenzene (TCB) (4.4 g, 3.0 mL) were heated to 145°–150° C. for 5 hours. The reaction was monitored by GC area percent with the results shown below.

| Time | GC Area Percent | | | |
|---|---|---|---|---|
| | CNBTF | TCB | OBTNB | Conversion |
| 0.5 hrs | 50.7 | 44.9 | 1.49 | 2.9% |
| 1.5 hrs | 46.5 | 43.5 | 6.28 | 11.9% |

*TCB = 1,2,4-trichlorobenzene

The material was dissolved, after cooling, in methylene chloride (25 mL) and filtered to remove salts. The solution was analyzed by GC-ISTD which showed the presence of 1,1'-oxy-bis(3-trifluoromethyl-4-nitrobenzene) (1.8 g). Compare to Comparative Example 2.

COMPARATIVE EXAMPLE 1

1,1'-Oxy-bis(3-trifluoromethyl-4-nitrobenzene)

5-Chloro-2-nitrobenzotrifluoride (4.6 g, 20 mmol), 18-crown-6 (0.19 g, 0.71 mmol), and potassium carbonate (1.34 g, 10 mmol) were heated to 130°–135° C. The reaction was monitored by GC area percent with the results shown below.

| Time | GC Area Percent | | |
|---|---|---|---|
| | CNBTF | OBTNB | Conversion |
| 0.5 hrs | 94.7 | 0.18 | 0.2% |
| 2.0 hrs | 93.6 | 0.40 | 0.4% |
| 3.5 hrs | 91.1 | 0.40 | 0.4% |

Compare to Example 1.

COMPARATIVE EXAMPLE 2

5-Chloro-2nitrobenzotrifluoride (4.6 g, 20 mmol), 18-crown-6 (0.19 g, 0.71 mmol), potassium carbonate (1.33 g, 10 mmol), and 1,2,4-trichlorobenzene (4.4 g, 3.0 mL) were heated to 145°–150° C. for 5 hours. The reaction was monitored by GC area percent with the results shown below.

| Time | GC Area Percent | | | |
|---|---|---|---|---|
| | CNBTF | TCB | OBTNB | Conversion |
| 0.5 hrs | 53.1 | 44.3 | 0.05 | 0.1% |
| 1.5 hrs | 53.3 | 44.2 | 0.12 | 0.2% |

The material was dissolved, after cooling, in methylene chloride (25 mL) and filtered to remove salts. The solution was analyzed by GC-ISTD which showed the presence of 1,1'-oxy-bis(3-trifluoromethyl-4-nitrobenzene) (0.03 g). Compare to Example 2.

We claim:

1. A process for the preparation of 1,1'-oxy-bis(3-trifluoromethyl-4-nitrobenzene) which comprises reacting in a non-polar solvent or in the absence of a solvent a compound of the formula

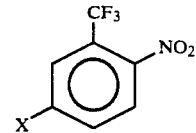

where X is F, Cl, Br, or I with up to a stoichiometric amount of an inorganic base selected from the group consisting of alkali metal hydroxides, alkali metal carbonates, and alkali metal bicarbonates, in the presence of a small amount of water, at least about 0.1 mole % of a benzoate catalyst and a phase transfer catalyst when a non-polar solvent is present.

2. A process according to claim 1 conducted in a non-polar solvent.

3. A process according to claim 2 wherein the inorganic base is sodium carbonate or potassium carbonate.

4. A processing according to claim 2 wherein the inorganic base is sodium hydroxide or potassium hydroxide.

5. A process according to claim 1 conducted in the absence of a solvent.

6. A process according to claim 5 wherein the inorganic base is sodium carbonate or potassium carbonate.

7. A process according to claim 5 wherein the inorganic base is sodium hydroxide or potassium hydroxide.

8. A process according to claim 1 wherein the reaction temperature is between about 110 and 220° C.

9. A process according to claim 1 wherein said benzoate catalyst is a benzoate ester of 4-nitro-3-trifluoromethylphenol.

10. A method of preparing 1,1'-oxy-bis(3-trifluoromethyl-4-nitrobenzene) comprising
(A) preparing a reaction mixture which comprises
(1) a compound having the formula

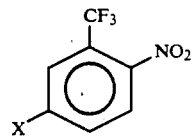

where X is F or Cl;
(2) up to a stoichiometric amount of sodium carbonate;
(3) at least about 0.1 mole % of benzoate catalyst selected from the group consisting of benzoic acid, chlorobenzoic acids, bromobenzoic acids, fluorobenzoic acids, dichlorobenzoic acids, dibromobenzoic acids, difluorobenzoic acids, tribromobenzoic acids, trichlorobenzoic acids, trifluorobenzoic acids, trifluoromethylbenzoic acids, nitrobenzoic acids, dinitrobenzoic acids, $C_1$ to $C_{12}$ alkylbenzoic acids, $C_1$ to $C_{12}$ alkoxybenzoic acids, $C_2$ to $C_{12}$ acyloxybenzoic acids, and salts thereof;
(4) a minimal amount of water;
(5) an optional non-polar solvent; and
(6) a phase transfer catalyst if said non-polar solvent is present; and
(B) heating said reaction mixture between about 110 and 220° C.

11. A process according to claim 10 wherein X is Cl.

* * * * *